US009719978B2

(12) United States Patent
Nedwed et al.

(10) Patent No.: US 9,719,978 B2
(45) Date of Patent: Aug. 1, 2017

(54) DETECTING OIL UNDER ICE

(71) Applicants: Timothy J. Nedwed, Houston, TX (US); Changyong Zhang, Conroe, TX (US); David A. Palandro, The Woodlands, TX (US)

(72) Inventors: Timothy J. Nedwed, Houston, TX (US); Changyong Zhang, Conroe, TX (US); David A. Palandro, The Woodlands, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 0 days.

(21) Appl. No.: 15/214,608

(22) Filed: Jul. 20, 2016

(65) Prior Publication Data

US 2017/0082593 A1 Mar. 23, 2017

Related U.S. Application Data

(60) Provisional application No. 62/219,717, filed on Sep. 17, 2015.

(51) Int. Cl.
*G01N 33/28* (2006.01)
*G01N 21/59* (2006.01)
*G01N 21/31* (2006.01)

(52) U.S. Cl.
CPC ......... *G01N 33/2823* (2013.01); *G01N 21/31* (2013.01); *G01N 21/59* (2013.01)

(58) Field of Classification Search
CPC .... G01N 33/5308; G01N 21/31; G01N 21/59; G01N 24/08; G01N 24/081; G01N 33/2823
See application file for complete search history.

(56) References Cited

U.S. PATENT DOCUMENTS

| 8,711,009 | B2 | 4/2014 | Broman et al. |
| 2011/0181279 | A1* | 7/2011 | Srnka ................ G01N 24/08 324/307 |
| 2011/0291862 | A1* | 12/2011 | Broman ................ B63C 11/42 340/984 |
| 2013/0099960 | A1 | 4/2013 | Broman et al. |
| 2014/0159936 | A1 | 6/2014 | Medlin et al. |
| 2014/0159937 | A1 | 6/2014 | Beadle et al. |

(Continued)

FOREIGN PATENT DOCUMENTS

WO   WO 2013/071185 A1   5/2013

OTHER PUBLICATIONS

Wilkinson, J., et al., "Capabilities for Detection of Oil Spills Under Sea Ice from Autonomous Underwater Vehicles," Arctic Oil Spill Response Technology Joint Industry Programme (JIP), Oct. 15, 2013.

*Primary Examiner* — Michael P Stafira
(74) *Attorney, Agent, or Firm* — ExxonMobil Upstream Research Company Law Dept.

(57) ABSTRACT

Methods and systems for detecting oil proximate to a body of ice is disclosed herein. An example system includes an energy emitter disposed proximate to a first surface of a body of ice. An energy detector is disposed proximate to a second surface of the body of ice. The energy detector is used to map a distribution of oil proximate to the body of ice based, at least in part, on differences in energy transmitted through the body of ice.

20 Claims, 6 Drawing Sheets

(56) References Cited

U.S. PATENT DOCUMENTS

2014/0159938 A1\* 6/2014 Shipley .................... G01V 3/12
 342/22
2014/0319076 A1\* 10/2014 Galushko ............... B63G 8/001
 210/747.6

\* cited by examiner

102

106

DETECTING OIL UNDER ICE

CROSS-REFERENCE TO RELATED APPLICATION

This application claims the benefit of U.S. Provisional Patent Application 62/219,717, filed Sep. 17, 2015, entitled DETECTING OIL UNDER ICE, the entirety of which is incorporated by reference herein.

FIELD

The present techniques relate generally to detecting oil proximate to ice, and more particularly, to a two vehicle remote system for detecting oil trapped under or within a body of ice.

BACKGROUND

This section is intended to introduce various aspects of the art, which may be associated with exemplary embodiments of the present techniques. This discussion is believed to assist in providing a framework to facilitate a better understanding of particular aspects of the present techniques. Accordingly, it should be understood that this section should be read in this light, and not necessarily as admissions of prior art.

The potential release of oil in a marine environment including ice has been of concern since the exploration and production for hydrocarbon resources in the Arctic began in the early 1970s. It is more challenging to detect oil under the ice surface, or trapped in ice layers, than to detect an oil slick on a water surface. There have been numerous efforts directed to detecting oil under ice using acoustical reflection, ultraviolet-visible (UV-Vis) reflectance, and ground penetrating radar, among others. All of these techniques have shown some capability to detect oil under ice.

However, the methods proposed to date may have a limited range of applicability and may be susceptible to giving false positive results. Many of these techniques require traversing across the ice surface, and some also require the removal of any snow cover to ensure good ice contact with a sensor. The surface access presents logistic issues, and may limits the coverage to a small area each day. One technique that provides a direct signal from oil is reflectance of ultraviolet and visible light from a surface of the ice, which provides an absorbance measurement. This technique, which may be termed transflectance, may be limited to the detection of oil at the surface or only a few millimeters below the surface of ice. Furthermore, transflectance may be limited by the presence of snow on the surface of the ice, which may scatter the incident and reflected light, obscuring the signal from oil.

A number of other techniques have been researched to detect the presence of oil under, on, or within ice. For example, U.S. Patent Application Publication No. 2011/0181279, by Srnka et al., discloses a techniques for detecting a liquid, such as a hydrocarbon, under a surface, such as ice, snow, or water. The method may be used in an arctic region to detect oil spills, leaks, or seepages. In the techniques, a nuclear magnetic resonance (NMR) tool with an antenna sends a radio-frequency (RF) excitation pulse or signal into volume of substances being detected. An NMR response signal is detected to determine the presence of the liquid of interest. The NMR response signal may include a relaxation time element and an intensity level and may include other NMR measurements, such as a free induction signal (T2*), a spin echo signal (T2), a train of spin echo signals (T2), or a thermal equilibrium signal (T1).

Further, U.S. Patent Application Publication No. 2014/0159936, by Medlin et al., discloses using coordinated airborne and ground platforms for detecting oil covered by ice. Detecting an oil mass covered by ice includes collecting data, such as synthetic-aperture radar data, using an airborne platform moved about a search area above the ice. Once an area that may have an oil mass covered by the ice is located based upon the data, confirmation data is collected using a ground platform moved over the alert area. The confirmation data may include wideband impulse radar data, acoustic sensor data, and light detection and ranging (LIDAR) data. An oil mass covered by the ice is detected based upon the confirmation data.

Further, International Patent Application No. WO2013/071185, by Pottorf et al., discloses a technique for the detection of hydrocarbons. The method includes deploying an underwater vehicle (UV) into a body of water and directing the UV to a target location. The UV collects measurement data within the body of water at the target location, which is then analyzed to determine whether hydrocarbons are present at the target location. The measurement data may include determining chemical composition, such as the concentration of hydrocarbon or non-hydrocarbon gases, pH, or oxidation state in the body of water. Further, physical measurements may be determined, such as magnetic anomalies or gravity.

A number of other research projects have focused on the use of unmanned underwater vehicles to detect oil spills under sea ice. Many of these are summarized in Wilkinson, J., T. Maksym, and H. Singh, "Capabilities for Detection of Oil Spills Under Sea Ice from Autonomous Underwater Vehicles," Arctic Oil Spill Response Technology Joint Industry Programme (JIP), 15 Oct. 2013.

The techniques described above are directed to measurements made from a single side of the sea ice. Any number of factors may lower the ability of these techniques to detect oil, such as oil trapped deep within layers of the sea ice.

SUMMARY

The present disclosure provides a system operable to detect oil proximate to a body of ice on a body of water. The system includes an energy emitter disposed proximate to a first surface of the body of ice. An energy detector is disposed proximate to a second surface of the body of ice. The energy detector is used to map a distribution of oil proximate to the body of ice based, at least in part, on differences in energy transmitted through the body of ice.

In another aspect, the present disclosure provides a method for detecting oil proximate to a body of ice. The method includes disposing an energy emitter proximate to a first surface of the body of ice. The method includes disposing an energy detector proximate to a second surface of the body of ice. A distribution of oil proximate to the body of ice is mapped based, at least in part, on differences in energy transmitted through the body of ice.

In yet another aspect, the present disclosure provides a method for detecting oil trapped in or under ice in a marine environment with an autonomous underwater vehicle (AUV) and an unmanned aerial vehicle (UAV). The method includes deploying the AUV under an ice surface and deploying the UAV above the ice surface at a location suspected of having trapped oil under, within, or on the ice. The AUV includes an energy emitter to transmit energy through water, sea ice, snow, air, and any combinations thereof. The UAV includes an energy detector used to measure the intensity of the transmitted energy to identify locations wherein oil is potentially trapped under the ice, within the ice, on the ice, and any combinations thereof.

DESCRIPTION OF THE DRAWINGS

The advantages of the present techniques are better understood by referring to the following detailed description and the attached drawings, in which.

DETAILED DESCRIPTION

Figure 1:
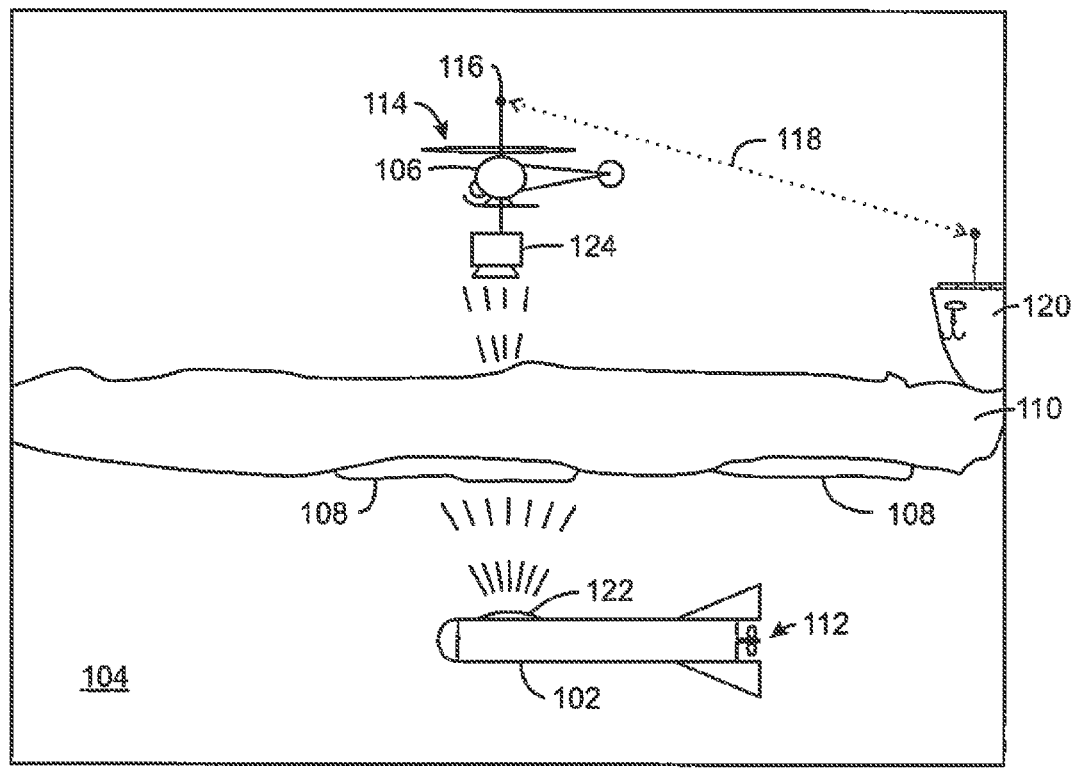
FIG. 1 is a schematic drawing of an oil detection system in accordance with one or more embodiments of the present disclosure.

In the following detailed description section, specific embodiments of the present techniques are described. However, to the extent that the following description is specific to a particular embodiment or a particular use of the present techniques, this is intended to be for exemplary purposes only and simply provides a description of the exemplary embodiments. Accordingly, the techniques are not limited to the specific embodiments described below, but rather, include all alternatives, modifications, and equivalents falling within the true spirit and scope of the appended claims.

Systems and methods described herein may be used to detect oil that has been trapped on, within, or under ice, such as sea ice, using an energy emitter on one side of the ice and an energy detector on the opposing side. The energy type and frequencies are selected to show differences in the amount of energy transmitted in the presence of oil. In one example, a light source may be used as the energy emitter and a camera may be used as the energy detector. In this example, the differences in the absorbance of the light can allow the location and quantification of oil contamination in, on, or under the sea ice.

In one or more embodiments, an autonomous underwater vehicle (AUV) may be coupled with an unmanned aerial vehicle (UAV) to detect the oil. The AUV may be equipped with an energy emitter, such as a high-powered strobe light, selected to generate frequencies for absorbance of the light by trapped oil and transmittance of the light through one or more of water, sea ice, snow, and air. The UAV may be equipped with an energy detector, such as a spectrometer, a digital camera, or a digital video camera, to measure the light intensity and wavelength immediately above the location of the AUV, while the light source of the AUV is activated. The UAV may include a global positioning system (GPS) to allow the measurements collected to be georeferenced. The UAV may also be equipped with communication equipment that allows the collected light intensity measurements to be sent back to a base station. The UAV may also physically transport the light intensity measurement data back to the base station for analysis.

The intensity of the energy, such as light, which is transmitted through the water, ice, snow, and/or air above, or below, the ice surface will allow the amount of oil to be mapped. Generally, any oil that is trapped on, in, or under the ice will absorb more of the light than would occur in the absence of oil. In this case, the light sensing device will measure less intense light when compared to a similar location without oil.

The use of the unmanned vehicles provides a number of advantages. For example, the unmanned AUVs and UAVs are less expensive than manned devices. Further, the UAVs and AUVs can be small enough to launch from vessels that aren't equipped to handle manned crafts, such as service boats or tugs. In addition, one oil spill response vessel or ground base can be a take-off and landing site, e.g., a base station, for multiple UAVs and AUVs.

At the outset, and for ease of reference, certain terms used in this application and their meanings as used in this context are set forth. To the extent a term used herein is not defined below, it should be given the broadest definition persons in the pertinent art have given that term as reflected in at least one printed publication or issued patent. Further, the present techniques are not limited by the usage of the terms shown below, as all equivalents, synonyms, new developments, and terms or techniques that serve the same or a similar purpose are considered to be within the scope of the present claims.

As used herein, an acoustic emitter is a device that emits sound waves or sound. The sound may be in the audible frequency range or may be above the audible frequency range.

As used herein, "proximate" indicates that an item is close to another item. The item that is proximate may be underneath the other item or over the other item.

As used herein, "substantially" or other words of degree are relative modifiers intended to indicate permissible variation from the characteristic so modified. It is not intended to be limited to the absolute value or characteristic which it modifies, but rather possessing more of the physical or functional characteristic than its opposite, and preferably, approaching or approximating such a physical or functional characteristic.

FIG. 1 is a schematic drawing of an oil detection system 100 in accordance with one or more embodiments. In the oil detection system, an AUV 102 is disposed in a body of water 104, and is in communication with an airborne device, such as a UAV 106. The coupled system can be deployed to a location in which oil 108 is suspected to be trapped on, under, or within a body of ice 110, e.g., a region of oil contamination. Working in tandem, the AUV 102 and the UAV 106 may detect and map the oil 108, for example, by the absorbance of light. The AUV 102 is described in more detail with respect to FIG. 4 and the UAV 106 is described in greater detail with respect to FIG. 5.

The AUV 102 may include propulsion components 112 to navigate in the body of water 104. Similarly, the UAV 106 may include flight components 114 to maintain the device airborne and navigate above the body of ice 110. In addition, the UAV 106 may be equipped with a base communication system 116 that is in communication 118 with a base station 120, such as a surface vessel, a drilling platform, or a land installation, among others. The underwater device may be equipped with an energy emitter, for example a light source 122, such as a high-powered strobe light, a laser source, or any number of other light sources. The airborne device may be equipped with an energy detector, for example a light detection device 124, such as a high-definition camera, a spectrometer, or any number of other sensing devices. In other embodiments, the underwater device may be equipped with the energy detector and the airborne device may be equipped with the energy emitter.

The techniques are not limited to the arrangement shown, for example, the light source may be on the UAV and the light sensing system on the AUV. With this configuration the UAV will be the light emitting source and the AUV will be the light sensing platform. In addition, the light source 122 may be replaced by other energy emitters, such as an acoustic source or a radio source, among others. In these embodiments, the light detection device 124 will also be replaced, for example, with an acoustic detector or a radio receiver, among others.

The location of the oil 108 with respect to the body of ice 110 may be more complex than the simplified schematic of FIG. 1. The body of ice 110 may include a plurality of layers. In many cases, the oil 108 does not form a single layer immediately below a single layer of ice 110, but is trapped within layers of ice or between layers of ice, as described with respect to FIG. 2.

Figure 2:
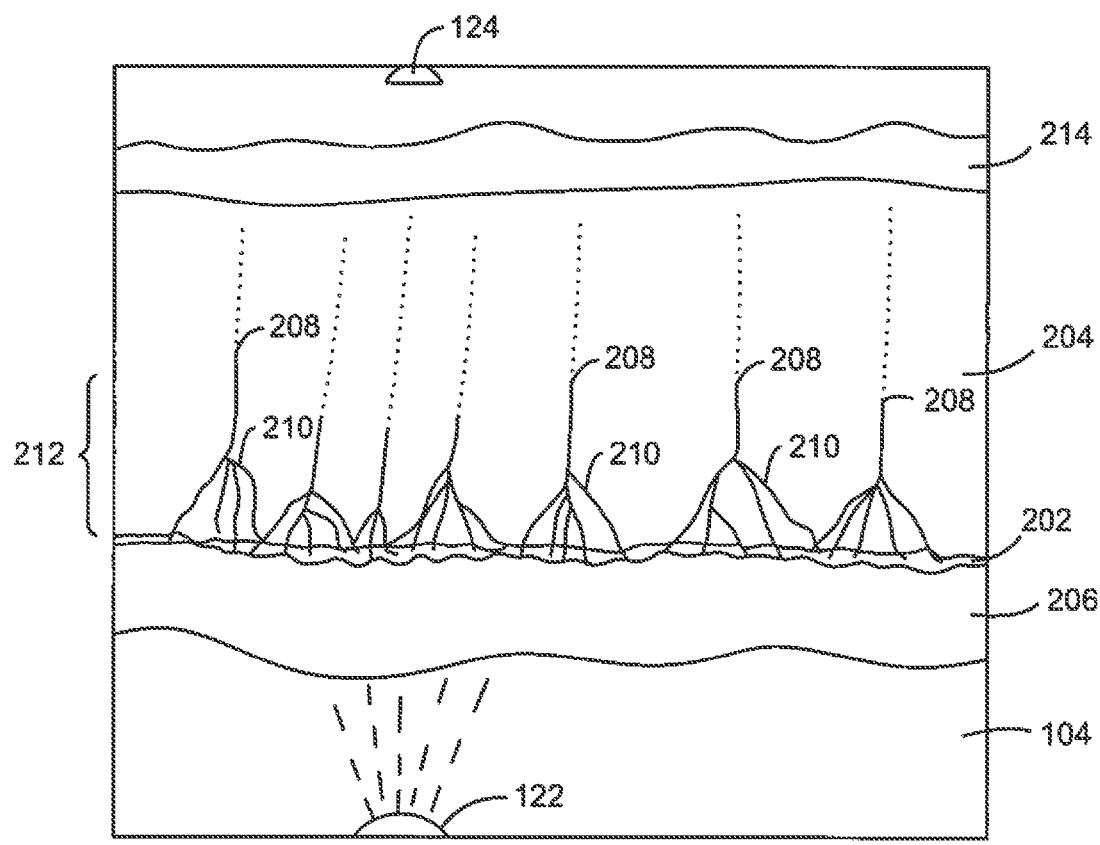
FIG. 2 is a close up cross sectional view of the detection of oil trapped between an older layer of ice and a newer layer of ice, in accordance with one or more embodiments of the present disclosure.

FIG. 2 is a close up cross sectional view of the detection of oil 202 trapped between an older layer of ice 204 and a newer layer of ice 206, in accordance with one or more embodiments. Like numbered items are as described with FIG. 1. As ice freezes over water in a marine environment, salt is forced out of the developing crystal structure of the ice, concentrating in droplets 208, for example, in the older layer of ice 204. As these droplets 208 have a lower freezing point than the surrounding ice, they will melt through the freezing layer, forming branched structures 210, similar to river deltas, as they exit the older layer of ice 204. At the bottom of the older layer of ice 204, a slush zone 212 may form while the ice is freezing.

Oil 202 that has spilled below the older layer of ice 204 may travel up the channels of the branched structures 210 and be trapped throughout the slush zone 212. Thus, techniques that are based on measurements taken only from one side or the other of the ice may not penetrate far enough into the older layer of ice 204 to detect or accurately measure the oil 202.

Further, as freezing continues, the newer layer of ice 206 may form, covering the oil 202. The newer layer of ice 206 may be too thick for light to penetrate, reach the oil, and reflect back to an AUV located in the body of water 104. Similarly, a layer of snow 214, or other surface effects, may make measurements from the top of the older layer of ice 204 ineffective.

In contrast, the present techniques measure energy that is transmitted through the ice formed, including the newer layer of ice 206, the oil 202, and the older layer of ice 204. Thus, a more accurate map of the locations and total amounts of oil may be generated.

Figure 3A:
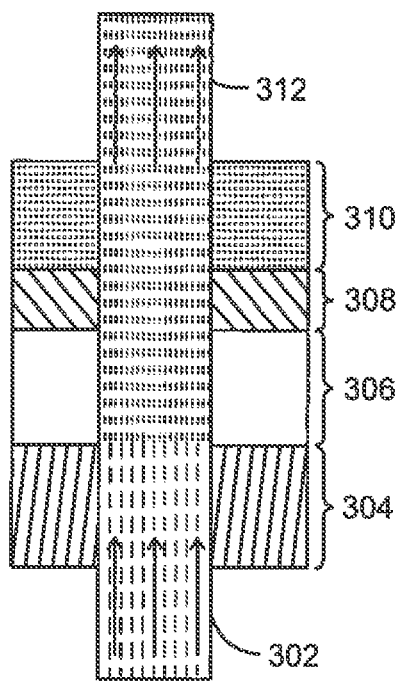
FIGS. 3A and 3B are side cross sectional diagrams of adsorption by oil trapped under or within layers of ice, in accordance with one or more embodiments of the present disclosure.
Figure 3B:
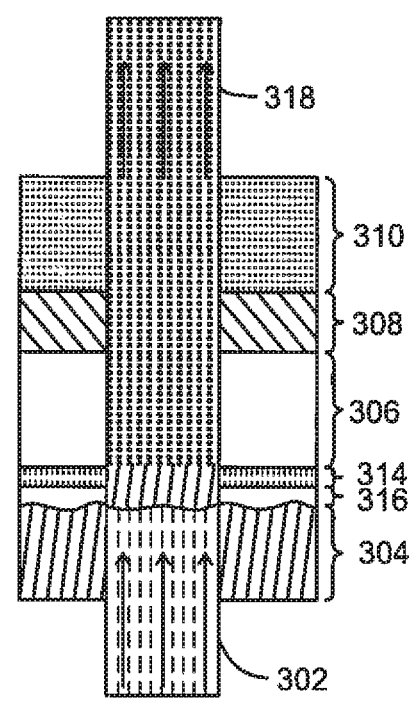

FIGS. 3A and 3B are side cross sectional diagrams of adsorption by oil trapped under or within layers of ice, in accordance with one or more embodiments. In FIG. 3A, the incident light ($I_0$) 302 passes through water 304, ice 306, snow 308, and air 310. The resulting transmitted light (I) 312 depends on the absorbance and scattering from each of these layers.

The absorbance of light by different substances may be described by the Lambert-Beer law, as shown in Eqn. 1.

$$A = -\log\left(\frac{I}{I_0}\right) \quad \text{Eqn. 1}$$

In Eqn. 1, A is the absorbance, $I_0$ is the intensity of the incidental light, and I is the intensity of the transmitted light. The absorbance is dependent on the substance or substances the light is penetrating and the wavelength of the incident light.

In FIG. 3B, oil 314 has been trapped under the ice 306, and another layer of ice 316 has formed under the oil 314. The wavelength or wavelengths of the light source may be selected so that oil 314 will absorb proportionally more light than the other substances. Because of this, light 318 transmitted through a location that includes oil 314 in addition to water 304, ice 306 and 316, snow 308, and air 310 will be less intense than light transmitted through water 304, ice 306, snow 308, and air 310 alone.

Figure 4:
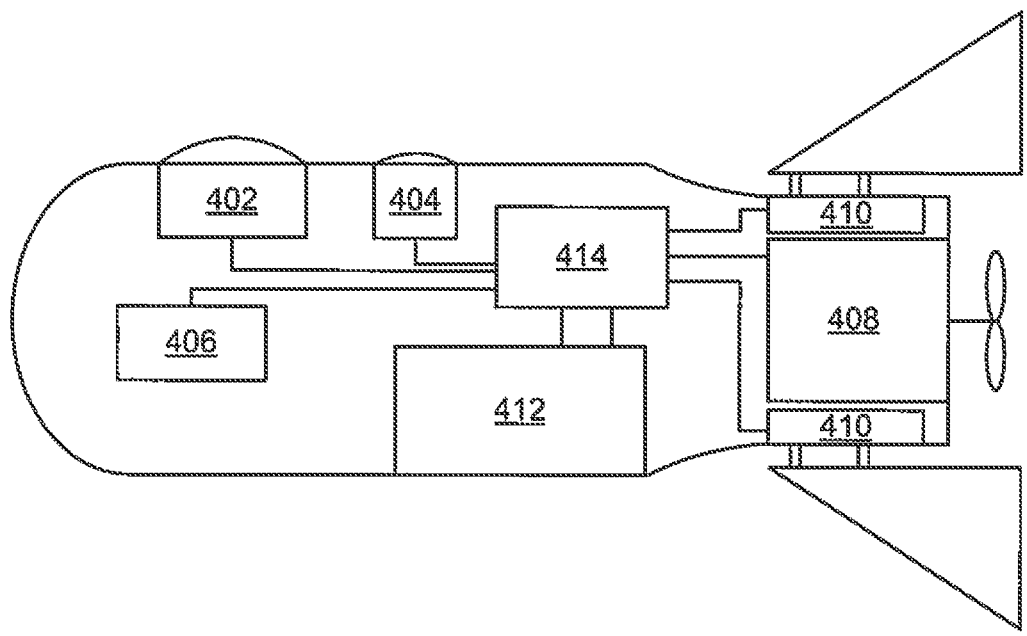
FIG. 4 is block diagram of an AUV, in accordance with one or more embodiments of the present disclosure.

FIG. 4 is block diagram of an AUV 102, in accordance with one or more embodiments. Like numbered items are as discussed with respect to FIG. 1. The AUV 102 may be any type of remotely controlled underwater vehicle that is selected for the environmental conditions, for example, capable of enduring near freezing salty water. For example, commercial AUVs may be available from Kongsberg Maritime of Kongsberg, Norway, and may include various vehicles, such as the HUGIN or MUNIN lines, among others. Another supplier of commercial AUVs that may be used is Teledyne Gavia ehf. of Kópavogur, Iceland. The AUVs available from Teledyne Gavia may include a number of interchangeable modules for communications, propulsion, navigation, power, and the like. Other suppliers may have similar products available.

Although the AUV 102 may be an autonomous vehicle such as the unmanned submarine vehicle shown in FIG. 4, other configurations may be used. For example, the autonomous underwater vehicle may be a positive buoyancy device, e.g., a buoyant under-ice rover, designed to travel along the underside of a body of ice.

The AUV 102 may include an energy emitter 402, such as a light source, a radio source, or an acoustic generator, among others. If the energy emitter 402 is a light source, any number of types may be selected that are capable of generating the appropriate wavelengths for higher absorbance by the entrapped or floating hydrocarbon than the surrounding ice and water. Further, the light source may be adjustable to utilize the characteristics of a specific wavelength or multiple wavelengths, such as ultraviolet, visible, or infrared, depending on ice and snow conditions. The light source may be intermittent, such as a strobe light, or continuous, such as a laser.

The UAV communication system 404 of the AUV 102 may be used to communicate with a paired UAV 106 (FIG. 1). The UAV communication system 404 may be an acoustic transceiver or a radio transceiver, which is separate from the energy emitter 402. For example, acoustic modems that may be used for the UAV communication system 404 include the Teledyne Benthos series, available from Teledyne Benthos of Cape Cod, Mass., USA.

Radio communications technologies may be used for the UAV communication system 404, for example, if the AUV is operating at a shallow depth under the ice. Such technology may include a spread spectrum ISM (industrial scientific medical) frequency radio transceiver working in the gigahertz frequencies. Although such systems may be used for communications that have significant spatial separation, such as several miles in air, the range may be much lower in water. However, the location of the UAV over the AUV 102 may allow such communications to take place. ISM communication units are available from any number of suppliers, such as the XBee® and XBee Pro® RF modules in the ZigBee® series or the Digi XLR PRO™ RF system, available from Digi International® Inc. of Minnetonka, Minn., USA. The radio frequency technologies may allow integration of the AUV 102 into a computer network, for example, with the UAV 106 functioning as a signal router to communicate with the base station.

The UAV communication system 404 may be integrated with the energy emitter 402, for example, through a digital pulsing of a light source or modulation of other energy emissions, such as acoustic signals. In these examples, the UAV communication system 404 may include a separate antenna or detector, such as a photodiode or phototransistor based detector, to receive signals from the UAV.

A navigation system 406 may be used to locate the AUV 102 in the water column and underneath the UAV. The navigation system 406 may use pressure gauges, accelerometers, or sonar, among others, to determine the location of the AUV. For example, the navigation system may be an inertial navigation system (INS), such as the Kearfott T24, the Kearfott T16 and the IxBlue ROVINS-90 available from Teledyne Gavia ehf. of Kópavogur, Iceland. Further, data from the UAV, such as a location determined by a GPS, may be used by the navigation system 406.

Other systems may be included to provide the functionality to the AUV 102. These include a propulsion system 408 that may be used to move the AUV 102 through the water column. The propulsion system 408 may include a system for adjusting the buoyance of the AUV 102, for example, if the AUV 102 is stopped in the water for more detail measurements. A steering system 410 may be used to steer the AUV 102 in the water column. A power supply 412 may power the AUV 102. The power supply 412 may include batteries, fuel cells, and other sources.

An AUV control system 414 may direct the operations of the AUV 102. This may include establishing communications with the UAV 106, as discussed with respect to FIG. 1. The AUV control system 414 may be an embedded computer system with specific modules for controlling various function. For example, such a system is available from Teledyne Gavia ehf. of Kópavogur, Iceland, as an integrated part of their AUV offerings. In this example, the system functions using a "virtual crew" paradigm in which different modules function as captain, engineer, and pilots, among others. Specialist pilots, e.g., modules to carry out particular functions, may be programmed or added to carry out additional functions, such as the functions to map oil in ice layers, described herein. Similar systems are available from other suppliers of AUVs, such as Kongsberg Maritime of Kongsberg, Norway.

The AUV control system 414 may initiate communications with the UAV. The AUV control system 414 may also use the propulsion system 408 and steering system 410 to maintain the AUV 102 in a position substantially underneath the UAV 106. The AUV control system 414 may be separate from, or embedded in, the navigation system 406. The AUV control system 414 may be coupled to the UAV communication system 404 to accept commands from the UAV, such as to activate the energy emitter 402 for measurements, or to deactivate the energy emitter 402, for example, to save energy. The AUV control system 414 may use the communications link with the UAV 106 to relay status updates to a base station or to accept commands from a base station, such as a command to return to the base station.

If the AUV 102 includes an energy detector, such as a camera, a high resolution camera, an acoustic detector, or other energy detector, the AUV control system 414 may generate a map, or image, of the distribution of oil in the ice. This may be performed, for example, by sending a command to the UAV to activate a light source, such as a strobe while a camera collects the image of the illuminated ice layers. This may be used in situations in which there is a substantial amount of ambient light above the ice, making a camera on the UAV less effective. The image may be transferred to the UAV 106 for relaying to the base station, or may be returned to the base station when the AUV 102 is recovered. Any number of other systems can be included in the AUV 102 for operations, such as sampling systems, upward directed sonar systems, magnetometer, or gravimeters, among others.

Figure 5:
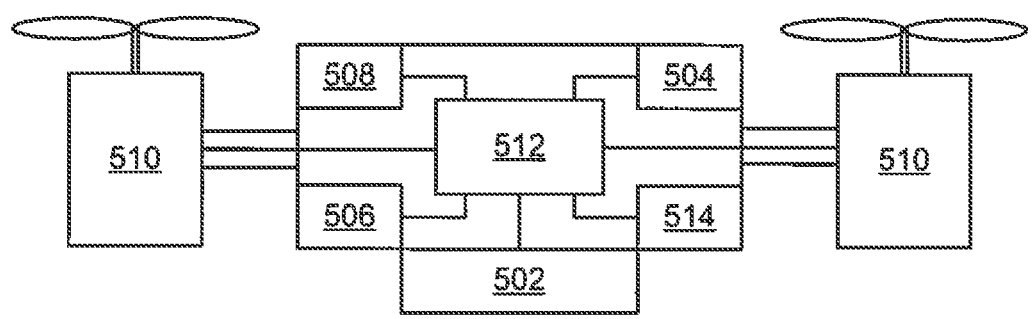
FIG. 5 is a block diagram of a UAV, in accordance with one or more embodiments of the present disclosure.

FIG. 5 is a block diagram of a UAV 106, in accordance with one or more embodiments. Like numbered items are as described with respect to FIG. 1. Any number of types of aerial vehicles may be used, including, for example, a drone, an unmanned helicopter, an unmanned airplane, or an unmanned dirigible as the remote control airborne device. In some cases, a manned aerial vehicle may be used, for example, if the detection and mapping were coincidental to another purpose. In this example, as the manned aircraft flies over the site, the AUV 102, as described herein, may establish communications and activate an energy emitter, such as a strobe light.

Although the component of the oil detection system that is located above the ice may be described as an aerial vehicle, it is understood that other vehicles may be used. For example, an unmanned rover designed for driving over ice may be used. In this case, the lower energy demands may allow for longer deployments, although at a higher risk if thin ice is encountered.

The UAV 106 may include an energy detector 502 to detect the energy from an energy emitter under a body of ice. The energy detector 502 may be light detector, an acoustic detector, or a radio detector, among others. For example, if the energy detector 502 is a light detector, it may be any detector capable of measuring the intensity of light at the wavelength or wavelengths produced by the light source. The light detector may include a high-definition camera, a video recorder, an infrared camera, a multi-spectral camera, a spectrophotometer, or any other light sensing device.

In addition, the UAV 106 may be equipped with a data communication system 504 that is in communication with a base station 120 (FIG. 1). The data communication system 504 may send images and video to a ground-based receiver at the base station 120, as well as accept commands from the ground based receiver. In one or more embodiments, the data communications system 504 may be an RF network product as described with respect to the UAV communication system 404 of an AUV 102 (FIG. 4). In this example, the RF network product may also be in communications with the UAV communication system 404 of the AUV 102, establishing a computer network with the AUV 102, the UAV 106, and the base station 120. In one or more embodiments, the data communication system 504 may include a satellite uplink system, for example, if the UAV/AUV pair is out of range of the base station 120. In one or more embodiments, a separate AUV communication system 506 may be included in the UAV 106 to communicate with the paired AUV 102, for example, on a different radio frequency, or using a different technology, such as a light emitter to transmit a digital data stream or an acoustic transceiver to couple to an acoustic modem. The data communications systems 504 and 506 may include and utilize any of a variety of known protocols to manage the exchange of information, such as TCP/IP, and the like.

A global positioning system (GPS) 508 may be used to provide an accurate position for the UAV 106. This may allow for the geo-referencing of an oil slick under ice. Further, the position data from the GPS 508 may be transmitted to the AUV 102 to assist in navigation of the AUV 102.

A propulsion system 510 may be used to move the UAV 106 above the ice and to keep the UAV 106 generally positioned over the AUV 102. The propulsion system 510 may include multiple motors and blades, such as in a drone-type craft. Other propulsion systems may be used, depending on the type of aerial vehicle selected.

A UAV control system 512 may be included to direct the operations of the UAV 106. The control system may be an embedded computer system that has software modules to implement the functionality described herein. For example, the control system may use the AUV communications system 506 to send a command to the AUV 102 to start the energy emitter. The UAV control system 512 may then use the energy detector 502 to detect the energy and create a map of the energy detected. The map may be a single image, or multiple images, that show the location of oil trapped under, on, or within ice. The UAV control system 512 may send the images back to a base station 120 using the data communications system 504. The UAV control system 512 may also use a power system 514, such as a battery or fuel cell, to power the propulsion system 510 and other units of the UAV 106.

The UAV 106 may be an autonomous craft, designed to complete a mission with minimal input, and automatically return to the base station, for example, when the data collection is completed or when power is running low. In other examples, the UAV 106 may be a remote controlled vehicle designed to accept commands directly from an operator at the base station and send images back to the base station. In this example, some local intelligence may be used to assist the operator in finding the AUV 102 and maintaining the position of the UAV 106 over the AUV 102.

Figure 6:
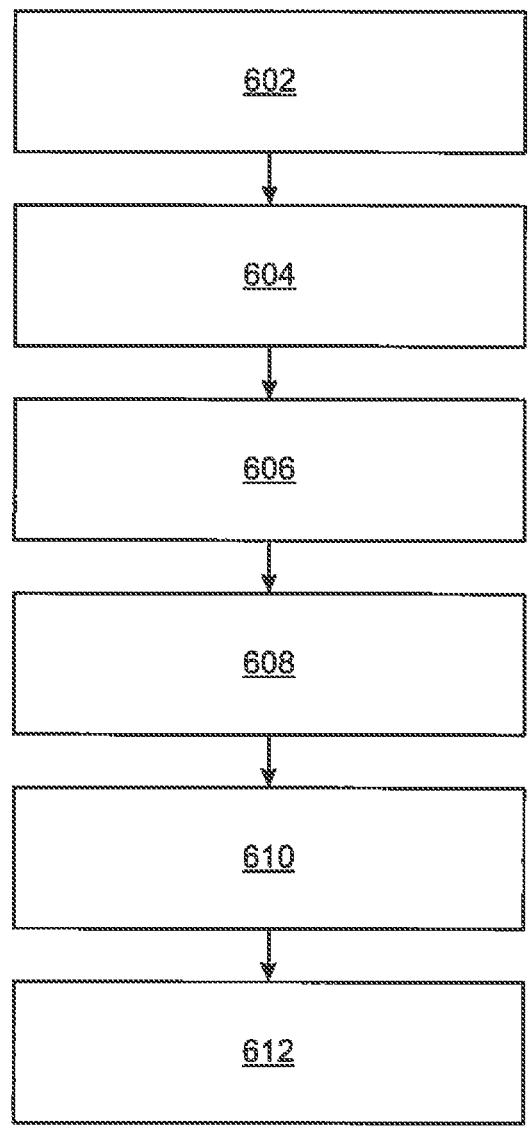
FIG. 6 is a process flow diagram of a method for detecting oil trapped under or within the body of ice, in accordance with one or more embodiments of the present disclosure.

FIG. 6 is a process flow diagram of a method 600 for detecting oil trapped on, under, or within layers of ice, in accordance with one or more embodiments. At block 602, an AUV is fitted with energy emitter, such as a high-powered light source, selected to have a higher absorbance by trapped oil. At block 604, a UAV is equipped with an energy detector, such as a camera, a video camera device, and the like. The UAV may also be equipped with a global positioning system (GPS) and communication equipment. At block 606, the AUV-UAV pair may be transferred to a base station for deployment, such as a larger vessel, an aerial platform, or a land installation, among others. At block 608, the AUV-UAV pair is deployed. The AUV is launched under the ice and the UAV is positioned in the air above the AUV. The pair will be synchronized and deployed by remote control or instructed to traverse a predetermined path to survey a potential spill site. At block 610, the energy emitter and energy detector are activated in the vicinity of the survey area, and the energy detector collect measurements of the energy transmitted through the ice. At block 612, the AUV-UAV pair move over the survey area, mapping any oil deposits and communicating with the ground-based or vessel-based command center of the base station for analysis. The UAV control system may be fitted with an analysis module to perform onboard analysis of the light intensity to identify potential areas with oil and transmit these locations to a central command center. For example, the analysis module may identify areas of darker absorbance in an image collected by a camera. The UAV control system may then move the UAV and the paired AUV to those areas for further imaging to determine the potential presence of oil.

While the present techniques may be susceptible to various modifications and alternative forms, the examples discussed above have been shown only by way of example. However, it should again be understood that the techniques is not intended to be limited to the particular examples disclosed herein. Indeed, the present techniques include all alternatives, modifications, and equivalents falling within the true spirit and scope of the appended claims.

What is claimed is:

1. A system operable to detect oil proximate to a body of ice, comprising:
   an energy emitter disposed proximate to a first surface of the body of ice; and
   an energy detector disposed proximate to a second surface of the body of ice, wherein a distribution of oil proximate to the body of ice is mapped based, at least in part, on differences in energy transmitted through the body of ice.

2. The system of claim 1, wherein the body of ice comprises a plurality of layers and oil is trapped between at least two layers of ice.

3. The system of claim 1, wherein
   the energy emitter comprises a light source; and
   the energy detector comprises a light detector, wherein the light detector measures an absorbance of light transmitted through the body of ice from the light source.

4. The system of claim 1, wherein
   the energy emitter comprises an acoustic emitter; and
   the energy detector comprises an acoustic detector, wherein the acoustic detector measures a sound transmitted through the body of ice from the acoustic emitter.

5. The system of claim 1, wherein the energy emitter comprises a high-powered strobe light.

6. The system of claim 1, wherein the energy emitter comprises a laser system.

7. The system of claim 1, comprising:
   an autonomous underwater vehicle (AUV) comprising the energy emitter; and
   an unmanned aerial vehicle (UAV) comprising the energy detector.

8. The system of claim 7, wherein the AUV comprises:
   a UAV communication system operable to communicate with the UAV;
   the energy emitter comprising a strobe light;
   a navigation system;
   a propulsion system; and
   a control system that uses the UAV communication system, the navigation system and the propulsion system to coordinate a position of the AUV with a position of the UAV.

9. The system of claim 7, wherein the UAV comprises:
   an AUV communication system operable to communicate with the AUV;
   a data communications system for communicating with a base station;
   the energy detector comprising a multispectral camera;
   a navigation system comprising a global positioning system;
   a propulsion system; and a control system that uses the AUV communication system, the navigation system and the propulsion system to coordinate a position of the UAV with a position of the AUV.

10. The system of claim 9, wherein the data communications system is operable to accept commands from the base station and transmit images to the base station.

11. The system of claim 9, wherein the global positioning system georeferences images.

12. A method for detecting oil proximate to a body of ice, comprising:
- disposing an energy emitter proximate to a first surface of the body of ice;
- disposing an energy detector proximate to a second surface of the body of ice; and
- mapping a distribution of oil proximate to the body of ice based, at least in part, on differences in energy transmitted through the body of ice.

13. The method of claim 12, comprising determining an amount of oil based, at least in part, on an absorbance measurement.

14. The method of claim 12, comprising determining an amount of oil based, at least in part, on a measurement of sound waves transmitted through the body of ice.

15. The method of claim 12, comprising:
- disposing a light source on an autonomous underwater vehicle (AUV) as the energy emitter;
- disposing a light detector on an unmanned aerial vehicle (UAV) as the energy detector;
- moving the UAV over the AUV; and
- detecting light from the light source at the light detector.

16. The method of claim 15, comprising:
- using a first technique to locate a region of oil contamination; and
- deploying the UAV and AUV to create the map of the distribution of the oil contamination.

17. A method for detecting oil trapped in or under ice in a marine environment with an autonomous underwater vehicle (AUV) and an unmanned aerial vehicle (UAV), comprising:
- deploying the AUV under an ice surface and the UAV above the ice surface at a location suspected of having trapped oil under, within, or on the ice, wherein the AUV comprises an energy emitter to transmit energy through water, sea ice, snow, air, and any combinations thereof; and
- measuring the intensity of the transmitted energy using an energy detector on the UAV to identify locations wherein oil is potentially trapped under the ice, within the ice, on the ice, and any combinations thereof.

18. The method of claim 17, comprising:
- coupling the AUV with the UAV for synchronized energy emission and detection;
- controlling movements of the AUV and UAV so that the UAV is substantially above the AUV;
- moving the UAV under the ice surface and the AUV above the ice surface with the energy emitter on and the energy detector measuring the intensity of the transmitted energy; and
- creating images that map a distribution of the trapped oil.

19. The method of claim 18, comprising using a global position system (GPS) on the UAV to georeference the images.

20. The method of claim 19, comprising sending the images from the UAV to a base station.

* * * * *